United States Patent
Hashimoto et al.

(10) Patent No.: US 8,110,589 B2
(45) Date of Patent: Feb. 7, 2012

(54) ECTOPARASITICIDE COMPOSITION AND A METHOD FOR EXTERMINATING EXTOPARASITES

(75) Inventors: Yosuke Hashimoto, Kanagawa (JP); Yoshiko Tamura, Kanagawa (JP); Mamoru Takiuchi, Kanagawa (JP); Hidenobu Yanase, Fukuoka (JP)

(73) Assignee: Kyoyu Agri Co., Ltd., Kanagawa (JP)

( * ) Notice: Subject to any disclaimer, the term of this patent is extended or adjusted under 35 U.S.C. 154(b) by 665 days.

(21) Appl. No.: 12/140,768

(22) Filed: Jun. 17, 2008

(65) Prior Publication Data

US 2009/0312378 A1    Dec. 17, 2009

(51) Int. Cl.
*A61K 31/41* (2006.01)
*A61K 31/42* (2006.01)

(52) U.S. Cl. .................................. 514/360; 514/375

(58) Field of Classification Search .............. 514/360, 514/375
See application file for complete search history.

(56) References Cited

FOREIGN PATENT DOCUMENTS

| JP | 9-59115 A | 3/1997 |
|---|---|---|
| JP | 2000-501695 A | 2/2000 |
| JP | 3189011 B2 | 7/2001 |
| JP | 2002-114604 A | 4/2002 |
| JP | 3574785 B2 | 10/2004 |
| WO | 93/22297 A1 | 11/1993 |
| WO | 96/41534 A1 | 12/1996 |

*Primary Examiner* — Sreeni Padmanabhan
*Assistant Examiner* — Renee Claytor
(74) *Attorney, Agent, or Firm* — Sughrue Mion, PLLC

(57) ABSTRACT

An ectoparasiticide composition for animals including etoxazole as an active ingredient, a UV absorber and a phenol antioxidant, and a method for exterminating ectoparasites using the composition. The preferable blending ratio between etoxazole, a UV absorber and a phenol antioxidant in terms of mass ratio is 1: from 0.05 to 5: from 0.05 to 5.

8 Claims, No Drawings

ECTOPARASITICIDE COMPOSITION AND A METHOD FOR EXTERMINATING EXTOPARASITES

TECHNICAL FIELD

The present invention relates to an ectoparasiticide composition and a method for exterminating ectoparasites. More specifically, the present invention relates to an ectoparasiticide composition increased in photostability, used on animals, and a method for exterminating ectoparasites using the composition.

BACKGROUND ART

Etoxazole((RS)-5-tert-butyl-2-[2-(2,6-difluorophenyl)-4,5-dihydro-1,3-oxazole-4-yl]phenetol) is oxazoline compound, already known as insecticide or miticide (Japanese patent No. 3189011 and Japanese patent No. 3574785) and also known as ectoparasiticide on animals and acaricide for monophagous mites (Japanese patent application Laid-Open No. 2000-501695). However, when used outdoors, photostability of oxazoline compound cannot be said to be satisfactory. Therefore, selection of photostabilizer is important.

In Japanese patent application Laid-Open No. H09-59115, imparting photostability to oxazoline compound is mentioned. But it is very much a situation in which even by using one of UV absorber selected from cyanoacrylate-type, benzotriazole-type and benzophenone-type or by using two or more of them in combination as described in the document, satisfactory photostability cannot be achieved.

Also, it is known that photostability is obtained by using a combination of 2,2',4,4'-tetrahydroxybenzophenone and 2,6-di-tert-butyl-4-(4,6-bis(octylthio)-1,3,5-triazine-2-ylamino)phenol (Japanese patent application Laid-Open No. 2002-114604), but it relates to suppressing of decomposition of pyrethroid agent and does not mention about oxazoline compound. Moreover, combination use of UV absorber and antioxidant having the same base cannot achieve sufficient suppression of photodecomposition of effective ingredients in agrichemicals. It describes that in many cases, only additive effects can be obtained and in some cases where the actions of the agents oppose each other, even reduction in effect of each agent can be observed.

DISCLOSURE OF INVENTION

Accordingly, the object of the present invention is to provide an ectoparasiticide composition having excellent photostability used on animals and a method for exterminating ectoparasites using the composition.

As a result of extensive studies on photostabilization of etoxazole, the present inventors have found that a composition where etoxazole is combined with UV absorber and phenol antioxidant can show synergetic effect in photostabilization. That is, by adding to etoxazole at least one kind of UV absorber and at least one kind of phenol antioxidant to thereby use these components in combination, stabilization effect against photodecomposition of etoxazole, which effect cannot be obtained when each of the components is used alone, can be obtained to thereby remarkably suppress photodecomposition of etoxazole. Further, the present inventors have found out that the effect against ectoparasites does not decrease and that its residual efficacy is markedly high, thereby completing the present invention.

That is, the present invention provides an ectoparasiticide composition and a method for exterminating ectoparasites using the composition, as follows.

1. An ectoparasiticide composition used on animals, comprising etoxazole as an active ingredient, UV absorber and phenol antioxidant.
2. The ectoparasiticide composition according to 1, wherein the UV absorber is one or more compounds selected from the group consisting of benzophenone compound represented by formula (I), cyanoacrylate compound represented by formula (II), benzotriazole compound represented by formula (III) and salicylic acid compound represented by formula (IV).

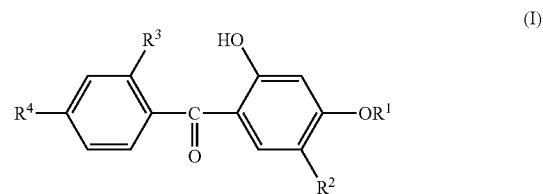
(I)

wherein $R^1$ represents a hydrogen atom, an alkyl group having 1 to 12 carbon atoms and a linear or branched chain, a benzyl group or a group represented by formula (1)

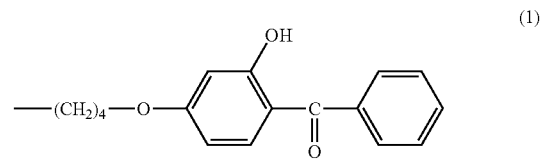
(1)

$R^2$ represents a hydrogen atom, a sulfo group ($SO_3H$) or a group represented by formula (2)

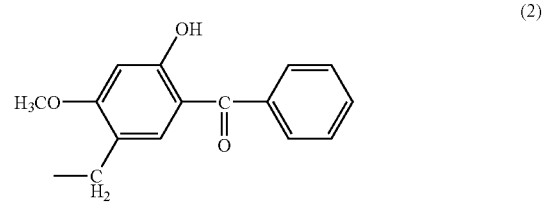
(2)

$R^3$ represents a hydrogen atom or a hydroxyl group, and $R^4$ represents a hydrogen atom or a methoxy group,

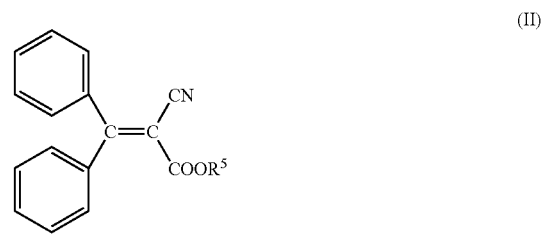
(II)

wherein $R^5$ represents an alkyl group having 1 to 8 carbon atoms and a linear or branched chain.

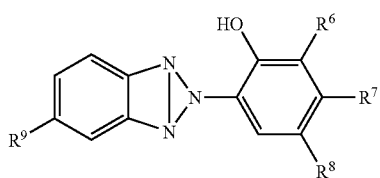

(III)

wherein $R^6$ represents a hydrogen atom, an alkyl group having 1 to 5 carbon atoms and a linear or branched chain, α,α'-dimethylbenzyl group, a group represented by formula (3) or a group represented by formula (4),

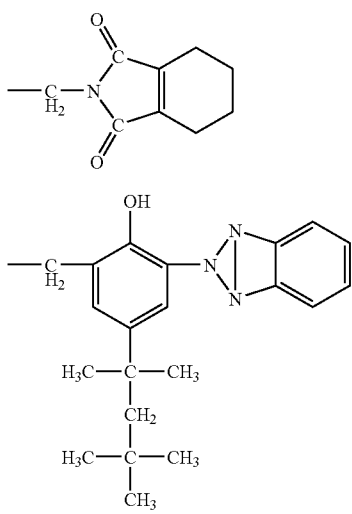

$R^7$ represents a hydrogen atom or an octoxy group, $R^8$ represents a hydrogen atom, an alkyl group having 1 to 8 carbon atoms and a linear or branched chain, a methoxy group, α,α'-dimethylbenzyl group or a methacryloxy group, $R^9$ represents a hydrogen atom or chlorine atom,

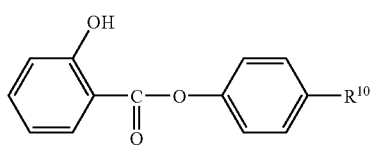

(IV)

wherein $R^{10}$ represents a hydrogen atom or a an alkyl group having 1 to 8 carbon atoms and a linear or branched chain.

3. The ectoparasiticide composition according to 1, wherein the phenol antioxidant is one or more compounds selected from the group consisting of a monophenol compound represented by formula (V) and the following compounds (1) to (13) which are bisphenol compound or polyphenol compound:

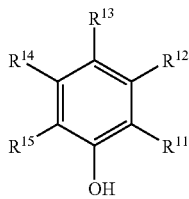

(V)

wherein $R^{11}$ represents a hydrogen atom, an isopropyl group, a chloromethyl group, a tert-butyl group, a benzyl group, 4-methylbenzyl group or a methylacrylate group; $R^{12}$ represents a hydrogen atom or a tert-butyl group; $R^{13}$ represents a hydrogen atom, a methyl group, ethyl group, a methoxy group, isooctyl propionate group or a stearyl propionate group; $R^{14}$ represents a hydrogen atom or a methyl group; $R^{15}$ represents a hydrogen atom or an alkyl group having 1 to 5 carbon atoms and a linear or branched chain;

(1) 2,2'-methylenebis(4-methyl-6-tert-butylphenol), (2) 2,2'-methylenebis(4-ethyl-6-tert-butylphenol), (3) 4,4'-thiobis(3-methyl-6-tert-butylphenol), (4) 4,4'-butylidenebis(3-methyl-6-tert-butylphenol), (5) 3,9-bis[1,1-dimethyl-2-[β-(3-tert-butyl-4-hydroxy-5-methylphenyl)propionyloxy]ethyl]-2,4,8,10-tetraoxaspiro[5.5]undecane, (6) 2,2-thiodiethylene bis[3-(3,5-di-tert-butyl-4-hydroxyphenyl)propionate], (7) triethyleneglycol bis[3-(3-tert-butyl-4-hydroxy-5-methylphenyl)propionate], (8) 1,6-hexanediol bis[3-(3,5-di-tert-butyl-4-hydroxyphenyl)propionate], (9) 1,1,3-tris(2-methyl-4-hydroxy-5-tert-butylphenyl)butane

(10) 1,3,5-trimethyl-2,4,6-tris(3,5-di-tert-butyl-4-hydroxybenzyl)benzene,

(11) tetrakis[methylene-3-(3,5-di-tert-butyl-4-hydroxyphenyl)propionate]methane,

(12) tris(3,5-di-tert-butyl-4-hydroxybenzyl)isocyanurate and

(13) bis[3,3'-bis(4'-hydroxy-3'-tert-butylphenyl)butyric acid] glycol ester.

4. The ectoparasiticide composition according to any one of 1 to 3, wherein the blending ratio between etoxazole, UV absorber and phenol antioxidant is in terms of mass ratio, 1: from 0.05 to 5: from 0.05 to 5.

5. A method for exterminating ectoparasites, using the ectoparasiticide composition according to any one of 1 to 4.

BEST MODE FOR CARRYING OUT THE INVENTION

The ectoparasiticide composition of the present invention contains etoxazole as effective ingredient and as photostabilizers, UV absorber and phenol antioxidant.

As for UV absorber, it is preferred that one or more compounds selected from the group consisting of benzophenone compound represented by formula (I), cyanoacrylate compound represented by formula (II), benzotriazole compound represented by formula (III) and salicylic acid compound represented by formula (IV) be used.

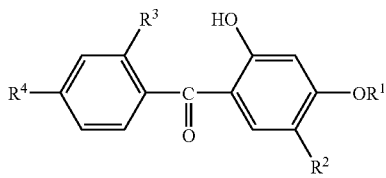

(I)

-continued

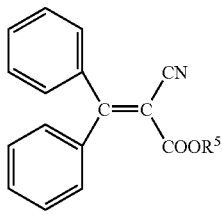
(II)

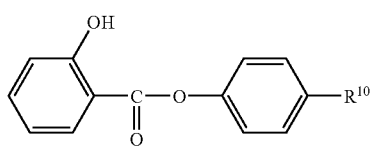
(III)

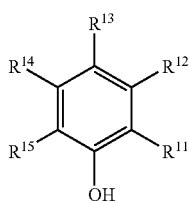
(IV)

As for phenol antioxidant, it is preferred that one or more compounds selected from the group consisting of a monophenol compound represented by formula (V) and bisphenol or polyphenol compound compounds be used.

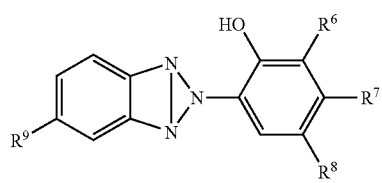
(V)

In the present invention, it is preferred that UV absorber consisting of one or more types selected from benzophenone compound(I), cyanoacrylate compound(II), benzotriazole compound(III) and salicylic acid compound(IV) and phenol antioxidant consisting of one or more types selected from monophenol compound(V) and bisphenol or polyphenol compound be used in combination.

In benzophenone compound, a UV absorber represented by formula (I), $R^1$ represents a hydrogen atom, an alkyl group having 1 to 12 carbon atoms and a linear or branched chain, a benzyl group or a group represented by formula (1),

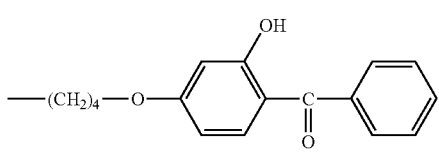
(1)

$R^2$ represents a hydrogen atom, a sulfo group or a group represented by formula (2),

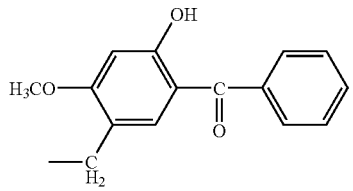
(2)

$R^3$ represents a hydrogen atom or a hydroxyl group, and $R^4$ represents a hydrogen atom or a methoxy group.

In cyanoacrylate compound represented by formula (II), $R^5$ represents an alkyl group having 1 to 8 carbon atoms and a linear or branched chain.

In benzotriazole compound represented by formula (III), $R^6$ represents a hydrogen atom, an alkyl group having 1 to 5 carbon atoms and a linear or branched chain, α,α'-dimethylbenzyl group, a group represented by formula (3) or a group represented by formula (4).

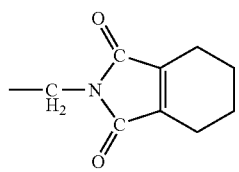
(3)

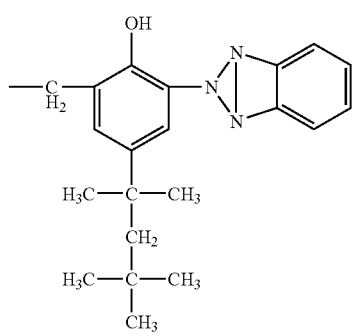
(4)

$R^7$ represents a hydrogen atom or an octoxy group, $R^8$ represents a hydrogen atom, an alkyl group having 1 to 8 carbon atoms and a linear or branched chain, a methoxy group, α,α'-dimethylbenzyl group or a methacryloxy group, $R^9$ represents a hydrogen atom or chlorine atom.

In salicylic acid compound represented by formula (IV), $R^{10}$ represents a hydrogen atom or a an alkyl group having 1 to 8 carbon atoms and a linear or branched chain.

In monophenol compound as a phenol antioxidant represented by formula (V), $R^{11}$ represents a hydrogen atom, an isopropyl group, a chloromethyl group, a tert-butyl group, a benzyl group, 4-methylbenzyl group or a methylacrylate group. $R^{12}$ represents a hydrogen atom or a tert-butyl group. $R^{13}$ represents a hydrogen atom, a methyl group, an ethyl group, a methoxy group, an isooctyl propionate group or a stearyl propionate group. $R^{14}$ represents a hydrogen atom or a methyl group. $R^{15}$ represents a hydrogen atom or an alkyl group having 1 to 5 carbon atoms and a linear or branched chain.

Examples of the bisphenol compound or polyphenol compound include:
(1) 2,2'-methylenebis(4-methyl-6-tert-butylphenol),
(2) 2,2'-methylenebis(4-ethyl-6-tert-butylphenol), (3) 4,4'-thiobis(3-methyl-6-tert-butylphenol),
(4) 4,4'-butylidenebis(3-methyl-6-tert-butylphenol),
(5) 3,9-bis[1,1-dimethyl-2-[β-(3-tert-butyl-4-hydroxy-5-methylphenyl)propionyloxy]ethyl]-2,4,8,10-tetraoxaspiro[5.5]undecane,
(6) 2,2-thiodiethylene bis[3-(3,5-di-tert-butyl-4-hydroxyphenyl)propionate],
(7) triethyleneglycol bis[3-(3-tert-butyl-4-hydroxy-5-methylphenyl)propionate],
(8) 1,6-hexanediol bis[3-(3,5-di-tert-butyl-4-hydroxyphenyl)propionate],
(9) 1,1,3-tris(2-methyl-4-hydroxy-5-tert-butylphenyl)butane,
(10) 1,3,5-trimethyl-2,4,6-tris(3,5-di-tert-butyl-4-hydroxybenzyl)benzene,
(11) tetrakis[methylene-3-(3,5-di-tert-butyl-4-hydroxyphenyl)propionate]methane,
(12) tris(3,5-di-tert-butyl-4-hydroxybenzyl)isocyanurate and
(13) bis[3,3'-bis(4'-hydroxy-3'-tert-butylphenyl)butyric acid] glycol ester.

Examples of UV absorber include the following compounds.

Benzophenone Compound:
Compound 1; 2,4-dihydroxybenzophenone,
Compound 2; 2-hydroxy-4-methoxybenzophenone,
Compound 3; 2-hydroxy-4-octoxybenzophenone,
Compound 4; 2-hydroxy-4-dodecyloxybenzophenone,
Compound 5; 2,2'-dihydroxy-4-methoxybenzophenone,
Compound 6; 2,2'-dihydroxy-4,4'-dimethoxybenzophenone,
Compound 7; 2-hydroxy-4-methoxybenzophenone-5-sulfonic acid trihydrate,
Compound 8; 4-benzyloxy-2-hydroxybenzophenone,
Compound 9; 2,2',4,4'-tetrahydroxybenzophenone,
Compound 10; 1,4-bis(4-benzoyl-3-hydroxyphenoxy)butane,
Compound 11; bis(2-methoxy-4-hydroxy-5-benzoylphenyl)methane.

Cyanoacrylate Compound:
Compound 12; 2-ethylhexyl-2-cyano-3,3'-diphenylacrylate,
Compound 13; ethyl-2-cyano-3,3'-diphenylacrylate.

Benzotriazole Compound:
Compound 14; 2-(2-hydroxy-5-methylphenyl)-2H-benzotriazole,
Compound 15; 2-(2-hydroxy-5-tert-butylphenyl)-2H-benzotriazole,
Compound 16; 2-(2-hydroxy-3,5-di-tert-butylphenyl)-2H-benzotriazole,
Compound 17; 5-chloro-2-(2-hydroxy-3-tert-butyl-5-methylphenyl)-2H-benzotriazole,
Compound 18; 5-chloro-2-(2-hydroxy-3,5-di-tert-butylphenyl)-2H-benzotriazole,
Compound 19; 2-2,2'-methylenebis-[4-(1,1,3,3-tetramethylbutyl)-6-(2H-benzotriazole-2-yl)phenol](2-hydroxy-3,5-di-tert-amylphenyl)-2H-benzotriazole,
Compound 20; 2-(2H-benzotriazole-2-yl)-4-methyl-6-(3,4,5,6-tetrahydrophthalimidylmethyl)phenol,
Compound 21; 2,2'-methylenebis[4-(1,1,3,3-tetramethylbutyl)-6-(2H-benzotriazole-2-yl)phenol],
Compound 22; 2-(2-hydroxy-4-octoxyphenyl)-2H-benzotriazole,
Compound 23; 2-(2-hydroxy-5-tert-octylphenyl)-2H-benzotriazole,
Compound 24; 2-(2-hydroxy-5-methacryloxyphenyl)-2H-benzotriazole,
Compound 25; 2-[2-hydroxy-3,5-bis(α,α'-dimethylbenzyl)phenyl]-2H-benzotriazole.

Salicylic Acid Compound:
Compound 26; phenyl salicylate,
Compound 27; p-tert-butylphenyl salicylate,
Compound 28; p-octylphenyl salicylate.

Among them, compound 2(=2-hydroxy-4-methoxy benzophenone) is preferred.

Examples of phenol antioxidant include the following compounds.
Compound A; 2-isopropyl-5-methylphenol(Another name: thymol),
Compound B; 2,6-diisopropyl-4-methylphenol,
Compound C; 2-benzyl-4,6-dimethylphenol,
Compound D; 2-chloromethyl-4,6-dimethylphenol,
Compound E; 2-(4-methylbenzyl)-4,6-dimethylphenol,
Compound F; methyl-3-(2-hydroxy-5-methoxyphenyl)acrylate,
Compound G; methyl-3-(2-hydroxy-3,5-dimethylphenyl)acrylate,
Compound H; methyl-3-(2-hydroxy-3-tert-butyl-5-methoxy phenyl)acrylate,
Compound I; 2,6-di-tert-butyl-4-methylphenol,
Compound J; 2,6-di-tert-butyl-4-ethylphenol,
Compound K; mixture of 2-tert-butyl-4-methoxyphenol and 3-tert-butyl-4-methoxyphenol,
Compound L; stearyl-3-( 3,5-di-tert-butyl-4-hydroxyphenyl)propionate,
Compound M; isooctyl-3-(3,5-di-tert-butyl-4-hydroxyphenyl)propionate,
Compound N; 2,2'-methylenebis(4-methyl-6-tert-butylphenol),
Compound O; 2,2'-methylenebis(4-ethyl-6-tert-butylphenol),
Compound P; 4,4'-thiobis(3-methyl-6-tert-butylphenol),
Compound Q; 4,4'-butylidenebis(3-methyl-6-tert-butylphenol),
Compound R; 3,9-bis[1,1-dimethyl-2-[β-(3-tert-butyl-4-hydroxy-5-methylphenyl)propionyloxy]ethyl]-2,4,8,10-tetraoxaspiro[5.5]undecane,
Compound S; 2,2-thiodiethylene bis[3-(3,5-di-tert-butyl-4-hydroxyphenyl)propionate],
Compound T; 1,1,3-tris(2-methyl-4-hydroxy-5-tert-butylphenyl)butane,
Compound U; 1,3,5-trimethyl-2,4,6-tris(3,5-di-tert-butyl-4-hydroxybenzyl)benzene,
Compound V; tetrakis[methylene-3-(3,5-di-tert-butyl-4-hydroxyphenyl)propionate]methane,
Compound W; triethylene glycol bis[3-(3-tert-butyl-4-hydroxy-5-methylphenyl)propionate],
Compound X; tris(3,5-di-tert-butyl-4-hydroxybenzyl)isocyanurate,
Compound Y; 1,6-hexanediol bis[3-(3,5-di-tert-butyl-4-hydroxyphenyl)propionate],
Compound Z; bis[3,3'-bis(4'-hydroxy-3'-tert-butylphenyl)butyric acid]glycol ester.

Among them, Compound I(=2,6-di-tert-butyl-4-methylphenol) is preferred.

In the present invention, the blending ratio between etoxazole:UV absorber:phenol antioxidant is, in terms of mass ratio, 1: from 0.05 to 5:from 0.05 to 5, preferably 1: from 0.1 to 1:from 0.1 to 1, more preferably 1: from 0.1 to 0.5: from 0.1 to 0.5. If the proportion of the UV absorber or the phenol antioxidant is too small, the synergetic effect in photostabilization brought out by combination use is difficult to obtain, while the proportions of the both components are too small, satisfactory photostabilization effect cannot be obtained. On the other hand, if the proportion of the UV absorber and/or phenol antioxidant is too large, it is disadvantageous from the economical viewpoint.

Further, the preferable blending ratio between UV absorber: phenol antioxidant is, in terms of mass ratio, 1: from 0.01 to 100, more preferably 1: from 0.05 to 20, still more preferably 1: from 0.1 to 10, particularly preferably 1: from 0.2 to 5.

The ectoparasiticide composition of the present invention contains etoxazole, and preferably at least one kind of compounds (1) to (28) and preferably at least one kind of compounds (A) to (Z).

Examples of animal on which the ectoparasiticide composition is used include livestock such as cows, sheep, goats and cocks and small animals such as dogs and cats.

The ectoparasiticide composition may be administered, in the form as produced, through a percutaneous route in an appropriate form of drug preparation or in form of molded product or may be applied to the environment surrounding the animal.

Percutaneous administration is carried out for example, by dipping, spraying, bathing, washing, dropping (pouring-on), coating, spotting or dusting. Among these, dropping (pouring-on) and spotting are preferred. Administration in form of molded product is carried out for example, by strips, plates, bands, ear tags or the like. Application to the environment is carried out for example by dusting, granule application, aerial application, spraying, fumigation, coating or the like. Among these, aerial application and spraying are preferred.

Examples of appropriate forms of drug preparation include, in case of molded products, strips, plates, bands and ear tags. Also, by adding liquid carrier or solid carrier and auxiliary substance, the composition may be used in drug formulation as oleum, ointment, gel, emulsion, suspension, oil-in-water type emulsified liquid agent, water-in-oil type emulsified liquid agent, water-dispersible agent, wettable granule, powdery agent, granules or the like.

Examples of liquid carrier include water, aliphatic or alicyclic hydrocarbons, such as liquid paraffin, isoparaffin, cyclohexane, naphthene and fumy kerosene; aromatic hydrocarbons such as xylene, trimethylbenzene, methylnaphthalene, dimethylnaphthalene, diisopropylnaphthalene and phenyl xylylethane; aliphatic alcohols such as methanol, ethanol, isopropanol, 2-ethylhexanol, n-octanol, isotridecyl alcohol, cetyl alcohol and oleyl alcohol; aromatic alcohols such as benzyl alcohol, phenyl ethanol and phenoxy ethanol; esters such as ethyl acetate, butyl acetate, methyl laurate, methyl caprate, methyl 2-ethylhexanoate, methyl oleate, isobutyl oleate and diisobutyl adipate; ketones such as methylethyl ketone and cyclohexanone; natural vegetable oils such as canola oil, soybean oil, safflower oil, rice oil, olive oil and palm oil; synthetic glycerides such as caprylic acid triglyceride, caprylic acid mono-diglyceride and caprylic/capric acid triglyceride; glycol ethers such as ethyleneglycol monobutyl ether, diethyleneglycol monobutyl ether, propyleneglycol monomethyl ether and propyleneglycol monobutyl ether; DMF; dimethyl acetamide; DMSO; and N-methyl-2-pyrrolidone.

Examples of solid carrier include natural mineral materials such as bentonite, talc, clay, attapulgite, sepiolite, acid clay, kaolin, diatom earth and calcium carbonate; and synthetic minerals such as alumina, white carbon, calcium silicate, sodium hydrogen carbonate, sodium sulfate and potassium chloride. Further, powders of organic substances such as sugars for example, lactose, sucrose and glucose, cellulose powder, cork powder, urea powder and flour can be used.

Examples of auxiliary agents include surfactant, dispersant or wetting agent, fixing agent, thickening agent, freezing stabilizer, binder, disintegrant, and stabilizer.

As the surfactant, dispersant and wetting agent, nonionic surfactant, anionic surfactant, amphoteric surfactant and the like may be used. Examples of nonionic surfactant include polyoxyalkylene alkyl ether, polyoxyalkylene polystyryl ether, polyoxyethylene castor oil, polyoxy. polyoxypropylene copolymer, polyoxyethylene mono.di.tri sorbitan fatty acid ester, polyoxyethylene sorbitol tetra oleate, monoaliphatic acid glyceride, monosorbitan fatty acid ester, sucrose fatty acid ester and alkyl glycoside. Examples of anionic surfactant include sodium alkylsulfate, sodium alkylbenzene sulfonate, calcium alkylbenzene sulfonate, sodium salt of dialkyl sulfosuccinate, naphthalene sulfonate, lignin sulfonate, phosphate salt or sulfate salt of polyoxyalkylene alkyl ether, phosphate salt or sulfate salt of polyoxyalkylene polystyryl ether, α-olein sulfonate salt and alkane sulfonate salt. Examples of amphoteric surfactant include disodium salt of N-lauryl-β-iminodipropionate and lecithin.

Examples of fixing agent include casein, gelatin, Arabic gum, a mixture of ammonium or sodium alginate and calcium carbonate, bentonite and polyvinyl alcohol.

Examples of thickening agent include heteropolysaccharides such as xanthan gum and rhamsan gum, celluloses or starch derivatives such as carboxymethyl cellulose, methyl cellulose, hydroxyethyl starch, polyvinyl alcohol, polyvinyl pyrrolidone, methylvinyl ether.maleic anhydride copolymer, montmorillonite-based clay mineral, smectite-based clay mineral, cation-modified montmorillonite-based clay mineral or smectite-based clay mineral, famed silica and alkyl-modified famed silica.

Examples of freezing stabilizer include ethylene glycol, propylene glycol and glycerine.

Examples of binder include celluloses or starch derivatives such as carboxymethyl cellulose, methyl cellulose, hydroxyethyl starch, and polyvinyl alcohols.

Examples of disintegrant include carboxymethyl cellulose, dextrin, sodium polyacrylate and isobutylene maleic anhydride copolymer.

Examples of stabilizer include PAP(diisopropyl phosphate), epoxylated soybean oil and tall oil fatty acid.

Examples of noxious organism on which the ectoparasiticide composition of the present invention can exhibit its effects include the followings:

Order Siphonaptera: Pulicidae, cat flea and

Order Acarina: Dermatophagoides such as *Dermatophagoides farinae* and *Dermatophagoides pteronyssinus*, flour mites such as cheese mite and brown legged grain mite, Glycyphagidaes such as *Glycyphagidae privatus, Glycyphagidae domesticus* and *Glycyphagidae destructor*, Cheyletidaes such as *Cheyletus malaccensis* and *Cheyletus fortis, Tarsonemidaes*, Chortoglyphidaes, *Haplochthonius simplex*, Ixodoidea such as *Haemaphysalis longicornis Neumann, Boophilus microplus*, Dermanyssidaes such as *Dermanyssus gallinae* and *Ornithonyssus* such as *Ornithonyssus sylviarum*.

In a case where the ectoparasiticide composition used on animals of the present invention is administered percutaneously or in form of molded product, it is appropriate that the amount is, in terms of etoxazole, within a range of 1 to 100 mg per 1 kg of body weight of the animal to be administered. In a case of applying the composition to the environment, the appropriate amount is within range of 2.5 to 250 mg/m$^2$ in terms of etoxazole.

EXAMPLES

Hereinafter, the present invention will be explained in more detail below with reference to examples and comparative examples, while citing the ectoparasiticide composition of the invention as preparation examples, and a stabilizing effect test and organism effect test as examination examples but the present invention is not restricted thereto. In addition, the term "part" in the preparation examples represents "part by mass".

Preparation Example 1

Oleum 1 part of etoxazole, 0.25 parts of compound (2) and 0.25 parts of compound I were dissolved in 10 parts of propylene glycol monobutyl ether, and the resultant was dissolved in 35 parts of caprylic triglyceride and 53.5 parts of liquid paraffin to prepare an oleum.

Preparation Example 2

Oily Suspension 4 parts of sorbitan monooleate and 1 part of polyoxyethylene sorbitan trioleate were dissolved in 91 parts of liquid paraffin uniformly and added thereto were 1 part of etoxazole, 0.25 parts of compound (1), 0.25 parts of compound L and 2.5 parts of cation modified montmorillonite type clay mineral followed by stirring and dispersing and thereafter, the mixture was wet milled by a beads-mill to prepare an oily suspension.

Preparation Example 3

Emulsion 5 parts of etoxazole, 1 part of compound (26), 1 part of compound C, 10 parts of polyoxyethylene tristyrylphenyl ether, 5 parts of calcium dodecylbenzenesulfonate and 78 parts of xylene were blended and dissolved uniformly to prepare an emulsion.

Preparation Example 4

Aqueous Suspension 5 parts of polyoxyethylene tristyrylphenyl ether phosphate, 20 parts of 1% aqueous solution of xanthan gum, 1 part of montmorillonite type clay mineral were dissolved and dispersed in 67 parts of water and 5 parts of etoxazole, 1 part of compound (3) and 1 part of compound E were stirred and dispersed thereto and, thereafter, the mixture was wet milled by a beads-mill to prepare an aqueous suspension.

The stabilizing effect and the organism effect of active ingredients of the present invention will next be explained in more detail with reference to the examination examples.

Examination Example 1

Stabilizing Effect Test of Etoxazole Oleum

According to Preparation Example 1, various types of oleums were prepared for Examples. Also, oleums were prepared as Comparative Examples by removing a UV absorber only, by removing phenol antioxidant only or by removing a UV absorber and a phenol antioxidant, from the Preparation Example 1. After 200 mg of the prepared oleum was applied to a glass petri dish having a diameter of 9 cm, the dish was left standing for two weeks or for a month under sunlight exposure. After that, 20 ml of n-hexane was placed in the glass petri dish to dissolve a sample, and 2 ml thereof was introduced to a Sep-Pak (registered trademark) Plus silica cartridge. Then, 5 ml of n-hexane was flowed thereto and the effluent was discharged. Next, 5 ml of ethyl acetate was flowed thereto and the effluent was collected to an egg plant flask. After the ethyl acetate was distilled away from the collected effluent by a rotatory evaporator, exactly 2 ml of acetonitrile was added to the residue dissolve it. The etoxazole was determined quantity by a high-performance liquid chromatography with a UV spectrophotometric detector. In addition, the decomposition rate by sunlight exposure was obtained using the following formula. Respective results were shown in Tables 1 and 2. The accumulated illuminances in 14 days or in one month were shown in respective tables of examination results. As seen from the above results, photostability of the etoxazole has been increased synergistically only when a UV absorber and a phenol antioxidant have been used in combination.

Decomposition rate(%)=(Amount of etoxazole before sunlight exposure−Amount of etoxazole after sunlight exposure)×100/Amount of etoxazole before sunlight exposure

TABLE 1

| | Oleum in Preparation Example 1 | | | Decomposition Rate (%) | |
|---|---|---|---|---|---|
| | UV Absorber | Antioxidant | Additive Amount (parts) | After 14 days | After one month |
| Example 1 | Compound (2) | Compound I | 0.25 + 0.25 | 2 | 10 |
| Example 2 | Compound (2) | Compound I | 0.25 + 0.50 | 1 | 5 |
| Example 3 | Compound (2) | Compound I | 0.10 + 1.00 | 3 | 6 |
| Example 4 | Compound (2) | Compound I | 1.00 + 0.10 | 8 | 15 |
| Example 5 | Compound (3) | Compound K | 0.25 + 0.25 | 8 | 9 |
| Example 6 | Compound (3) | Compound K | 0.25 + 0.50 | 3 | 5 |
| Example 7 | Compound (3) | Compound K | 0.10 + 1.00 | 4 | 6 |
| Example 8 | Compound (3) | Compound K | 1.00 + 0.10 | 10 | 18 |
| Example 9 | Compound (4) | Compound A | 0.25 + 0.25 | 8 | 15 |
| Example 10 | Compound (8) | Compound B | 0.25 + 0.25 | 1 | 4 |
| Example 11 | Compound (10) | Compound D | 0.25 + 0.25 | 2 | 6 |
| Example 12 | Compound (6) | Compound G | 0.25 + 0.25 | 1 | 3 |
| Comp. Ex. 1 | Compound (2) | — | 0.25 | 70 | 89 |
| Comp. Ex. 2 | Compound (2) | — | 1.0 | 60 | 80 |
| Comp. Ex. 3 | Compound (3) | — | 0.25 | 55 | 84 |
| Comp. Ex. 4 | Compound (3) | — | 1.0 | 52 | 79 |
| Comp. Ex. 5 | Compound (4) | — | 1.0 | 65 | 90 |

TABLE 1-continued

| | Oleum in Preparation Example 1 | | | Decomposition Rate (%) | |
|---|---|---|---|---|---|
| | UV Absorber | Antioxidant | Additive Amount (parts) | After 14 days | After one month |
| Comp. Ex. 6 | Compound (8) | — | 1.0 | 53 | 79 |
| Comp. Ex. 7 | Compound (10) | — | 1.0 | 70 | 91 |
| Comp. Ex. 8 | Compound (6) | — | 1.0 | 62 | 84 |
| Comp. Ex. 9 | — | Compound A | 1.0 | 15 | 50 |
| Comp. Ex. 10 | — | Compound B | 1.0 | 29 | 55 |
| Comp. Ex. 11 | — | Compound D | 1.0 | 21 | 48 |
| Comp. Ex. 12 | — | Compound G | 1.0 | 12 | 34 |
| Comp. Ex. 13 | — | Compound I | 0.25 | 79 | 84 |
| Comp. Ex. 14 | — | Compound I | 1.0 | 7 | 39 |
| Comp. Ex. 15 | — | Compound K | 0.25 | 77 | 89 |
| Comp. Ex. 16 | — | Compound K | 1.0 | 18 | 47 |
| Comp. Ex. 17 | — | — | — | 88 | 99 |

Accumulated illuminance: 6,050 kLx · hr forr 14 days and 14,120 kLx · hr for one month

TABLE 2

| | Oleum in Preparation Example 1 | | | Decomposition Rate(%) | |
|---|---|---|---|---|---|
| | UV Absorber | antioxidant | Additive Amount (parts) | After 14 days | After one month |
| Example 13 | Compound (14) | Compound N | 0.25 + 0.25 | 2 | 7 |
| Example 14 | Compound (15) | Compound U | 0.25 + 0.25 | 7 | 15 |
| Example 15 | Compound (16) | Compound Y | 0.25 + 0.25 | 10 | 18 |
| Example 16 | Compound (19) | Compound I | 0.25 + 0.25 | 3 | 5 |
| Example 17 | Compound (23) | Compound R | 0.25 + 0.25 | 8 | 9 |
| Example 18 | Compound (25) | Compound H | 0.25 + 0.25 | 5 | 10 |
| Example 19 | Compound (12) | Compound I | 0.25 + 0.25 | 4 | 6 |
| Example 20 | Compound (27) | Compound K | 0.25 + 0.25 | 3 | 8 |
| Comp. Ex. 18 | Compound (14) | — | 1.0 | 58 | 78 |
| Comp. Ex. 19 | Compound (15) | — | 1.0 | 61 | 81 |
| Comp. Ex. 20 | Compound (16) | — | 1.0 | 65 | 82 |
| Comp. Ex. 21 | Compound (19) | — | 1.0 | 66 | 87 |
| Comp. Ex. 22 | Compound (23) | — | 1.0 | 65 | 90 |
| Comp. Ex. 23 | Compound (25) | — | 1.0 | 60 | 85 |
| Comp. Ex. 24 | Compound (12) | — | 1.0 | 55 | 75 |
| Comp. Ex. 25 | Compound (27) | — | 1.0 | 62 | 84 |
| Comp. Ex. 26 | — | Compound N | 1.0 | 15 | 50 |
| Comp. Ex. 27 | — | Compound U | 1.0 | 21 | 55 |
| Comp. Ex. 28 | — | Compound Y | 1.0 | 21 | 48 |
| Comp. Ex. 29 | — | Compound I | 1.0 | 18 | 43 |
| Comp. Ex. 30 | — | Compound R | 1.0 | 25 | 61 |
| Comp. Ex. 31 | — | Compound H | 1.0 | 18 | 50 |
| Comp. Ex. 32 | — | Compound K | 1.0 | 15 | 45 |
| Comp. Ex. 33 | — | — | — | 84 | 99 |

Accumulated illuminance: 7,100 kLx · hr for 14 days and 13,540 kLx · hr for one month Examination Example 2

Stabilizing Effect Test of Etoxazole Oily Suspension

Various types of oily suspensions were prepared as Examples according to Preparation Example 2. Also, oily suspensions were prepared as Comparative Examples by removing a UV absorber only, by removing phenol antioxidant only, or by removing a UV absorber and a phenol antioxidant, from the Preparation Example 2. After 200 mg of the prepared oily suspension was applied to a glass petri dish having a diameter of 9 cm, the dish was left standing for two weeks or for one month under sunlight exposure. After that, 20 ml of n-hexane was placed on the glass petri dish to dissolve a sample, and 2 ml thereof was introduced to a Sep-Pak (registered trademark) Plus silica cartridge. Then, 5 ml of n-hexane was flowed thereto and the effluent was discharged. Next, 5 ml of ethyl acetate was flowed thereto and the effluent was collected to an egg plant flask. After the ethyl acetate was distilled away from the collected effluent by a rotatory evaporator, exactly 2 ml of acetonitrile was added to the residue to dissolve it. The etoxazole was determined quantity by a high-performance liquid chromatography with a UV spectrophotometric detector. In addition, the decomposition rate by sunlight exposure was obtained in the same manner as in Examination Example 1. The results were shown in Table 3. The accumulated illuminances in 14 days and in one month were shown in the table of examination results. As in the cases of tables 1 and 2, it is found that photostability of the etoxazole has been increased synergistically only when a UV absorber and a phenol antioxidant have been used in combination.

TABLE 3

| | Oily suspension of Preparation Example 2 | | | Decomposition Rate (%) | |
|---|---|---|---|---|---|
| | UV Absorber | Antioxidant | Additive Amount (parts) | After 14 days | After one month |
| Example 21 | compound (1) | compound L | 0.25 + 0.25 | 8 | 16 |
| Example 22 | compound (7) | compound M | 0.25 + 0.25 | 7 | 12 |
| Example 23 | compound (9) | compound P | 0.25 + 0.25 | 5 | 10 |
| Example 24 | compound (11) | compound X | 0.25 + 0.25 | 8 | 14 |
| Example 25 | compound (20) | compound Z | 0.25 + 0.25 | 8 | 18 |
| Example 26 | compound (28) | compound I | 0.25 + 0.25 | 3 | 8 |
| Example 27 | compound (18) | compound S | 0.25 + 0.25 | 6 | 11 |
| Example 28 | compound (20) | compound W | 0.25 + 0.25 | 9 | 17 |
| Comp. Ex. 34 | compound (1) | — | 1.0 | 58 | 78 |
| Comp. Ex. 35 | compound (7) | — | 1.0 | 61 | 81 |
| Comp. Ex. 36 | compound (9) | — | 1.0 | 65 | 82 |
| Comp. Ex. 37 | compound (11) | — | 1.0 | 66 | 87 |
| Comp. Ex. 38 | compound (20) | — | 1.0 | 65 | 90 |
| Comp. Ex. 39 | compound (28) | — | 1.0 | 60 | 85 |
| Comp. Ex. 40 | compound (18) | — | 1.0 | 55 | 75 |
| Comp. Ex. 41 | compound (20) | — | 1.0 | 62 | 84 |
| Comp. Ex. 42 | — | compound L | 1.0 | 35 | 70 |
| Comp. Ex. 43 | — | compound M | 1.0 | 28 | 64 |
| Comp. Ex. 44 | — | compound P | 1.0 | 20 | 48 |
| Comp. Ex. 45 | — | compound X | 1.0 | 22 | 55 |
| Comp. Ex. 46 | — | compound Z | 1.0 | 28 | 60 |
| Comp. Ex. 47 | — | compound I | 1.0 | 20 | 45 |
| Comp. Ex. 48 | — | compound S | 1.0 | 18 | 50 |
| Comp. Ex. 49 | — | compound W | 1.0 | 21 | 61 |
| Comp. Ex. 50 | — | — | — | 87 | 100 |

Accumulated illuminance; 6,220 kLx · hr for 14 days, 12,740 kLx · hr for one month Examination Example 3

Stabilizing Effect Test of Etoxazole Emulsion

Various types of emulsions were prepared as Examples according to Preparation Example 3. Also, emulsions were prepared as Comparative Examples, by removing a UV absorber only, by removing a phenol antioxidant only, or by removing a UV absorber and a phenol antioxidant, from the Preparation Example 3. After 1 g of the prepared emulsion was diluted by adding water so as to be 100 ml in total, 4 ml of the diluted solution was charged to a glass petri dish having a diameter of 9 cm followed by volatilizing water. Then, the dish was left standing for two weeks or for one month under sunlight exposure. After that, 20 ml of acetonitrile was placed on the glass petri dish to dissolve the sample, and the dissolved solution was collected to an egg plant flask. After the acetonitrile was distilled away by a rotatory evaporator, exactly 2 ml of acetonitrile was added to the residue to dissolve it. The etoxazole was determined quantity by a high-performance liquid chromatography with a UV spectrophotometric detector. In addition, the decomposition rate by sunlight exposure was obtained in the same manner as in Examination Example 1. The results were shown in Table 4. The accumulated illuminances in 14 days or in one month were shown in the table of the examination results. As in the cases of tables 1, 2 and 3, it is found that photostability of the etoxazole has been increased synergistically only when a UV absorber and a phenol antioxidant have been used in combination.

TABLE 4

| | Emulsion in Preparation Example 3 | | | Decomposition Rate (%) | |
|---|---|---|---|---|---|
| | UV Absorber | Antioxidant | Additive Amount (parts) | After 14 days | After one month |
| Example 29 | compound (26) | compound C | 1.0 + 1.0 | 4 | 7 |
| Example 30 | compound (2) | compound I | 1.0 + 1.0 | 3 | 6 |
| Example 31 | compound (5) | compound O | 1.0 + 1.0 | 5 | 9 |
| Example 33 | compound (17) | compound Q | 1.0 + 1.0 | 6 | 13 |
| Example 34 | compound (16) | compound J | 1.0 + 1.0 | 6 | 9 |
| Comp. Ex. 51 | compound (26) | — | 5.0 | 50 | 75 |
| Comp. Ex. 52 | compound (2) | — | 5.0 | 48 | 70 |
| Comp. Ex. 53 | compound (5) | — | 5.0 | 53 | 82 |
| Comp. Ex. 54 | compound (17) | — | 5.0 | 65 | 86 |
| Comp. Ex. 55 | compound (16) | — | 5.0 | 65 | 81 |
| Comp. Ex. 56 | — | compound C | 5.0 | 17 | 40 |
| Comp. Ex. 57 | — | compound I | 5.0 | 10 | 38 |
| Comp. Ex. 58 | — | compound O | 5.0 | 15 | 45 |
| Comp. Ex. 59 | — | compound Q | 5.0 | 20 | 50 |

TABLE 4-continued

| Emulsion in Preparation Example 3 | | | Decomposition Rate (%) | |
|---|---|---|---|---|
| UV Absorber | Antioxidant | Additive Amount (parts) | After 14 days | After one month |
| Comp. Ex. 60 | — | compound J | 5.0 | 15 | 42 |
| Comp. Ex. 61 | — | — | — | 87 | 99 |

Accumulated illuminance: 7,530 kLx · hr for 14 days and 14,180 kLx · hr for one month

Examination Example 4

Stabilizing Effect Test for Etoxazole Aqueous Suspension

Various types of aqueous suspensions were prepared as Examples according to Preparation Example 4. Also, aqueous suspensions were prepared as Comparative Examples by removing a UV absorber only, by removing a phenol antioxidant only, or by removing a UV absorber and a phenol antioxidant, from the Preparation Example 4. After 1 g of the prepared aqueous suspension was diluted by adding water so as to be 100 ml in total, 4 ml of the diluted solution was charged in a glass petri dish having a diameter of 9 cm followed by volatilizing water. Then, the dish was left standing for two weeks or for a month under sunlight exposure. After that, 20 ml of acetonitrile was placed in the glass petri dish to dissolve the sample, and the dissolved solution was collected to an egg plant flask. After the acetonitrile was distilled away by a rotatory evaporator, exactly 2 ml of acetonitrile was added to the residue to dissolve it. The etoxazole was determined quantity by a high-performance liquid chromatography with a UV spectrophotometric detector. In addition, the decomposition rate by sunlight exposure was obtained in the same manner as in Examination Example 1. The results were shown in Table 5. The accumulated illuminances in 14 days or in one month were shown in the table of the examination results. As in the cases of tables 1, 2, 3 and 4, it is found that photostability of the etoxazole has been increased synergistically only when a UV absorber and a phenol antioxidant have been used in combination.

Examination Example 5

Test of Organism Effect on *Haemaphysalis longicornis* Neumann

It is known that an etoxazole has an excellent ovicidal effect, a larvicidal effect and protonymph insecticidal effect, but no adulticidal effect. In this test, an initial effect and a residual efficacy were estimated by an ovicidal effect. On cattle, 1 ml per 10 kg of body weight of an oleum prepared in Preparation Example 1 or a oily suspension prepared in Preparation Example 2 was poured by an applicator. After 1 day of the treatment, female adult ticks were released to settle. Eggs were collected from the settled ticks which dropped by sucking cattle's blood and being gorged with the blood. The eggs were was stored at 25° c. for three weeks. After that, hatching status of the eggs were observed and hatching rate was obtained. Alternatively, after one month of outdoor rearing of the treated cattle, female adult ticks were released in the same way as in above. Then, hatching rates of the eggs laid by the adult ticks were obtained. As seen from the results, using a UV absorber and a phenol antioxidant in combination contributes to elongation of the residual efficacy of etoxazole as compared to using either of a UV absorber or a phenol antioxidant individually.

Hatching rate=(Number of hatched eggs/egg production)×100

TABLE 5

| Aqueous suspension in Preparation Example 4 | | | Decomposition Rate (%) | |
|---|---|---|---|---|
| UV Absorber | Antioxidant | Additive Amount (parts) | After 14 days | After one month |
| Example 35 | compound (3) | compound E | 1.0 + 1.0 | 5 | 10 |
| Example 36 | compound (21) | compound F | 1.0 + 1.0 | 7 | 15 |
| Example 37 | compound (22) | compound T | 1.0 + 1.0 | 10 | 18 |
| Example 38 | compound (24) | compound V | 1.0 + 1.0 | 3 | 5 |
| Example 39 | compound (13) | compound Z | 1.0 + 1.0 | 8 | 9 |
| Comp. Ex. 62 | compound (3) | — | 5.0 | 55 | 80 |
| Comp. Ex. 63 | compound (21) | — | 5.0 | 61 | 83 |
| Comp. Ex. 64 | compound (22) | — | 5.0 | 65 | 85 |
| Comp. Ex. 65 | compound (24) | — | 5.0 | 60 | 87 |
| Comp. Ex. 66 | compound (13) | — | 5.0 | 51 | 77 |
| Comp. Ex. 67 | — | compound E | 5.0 | 17 | 48 |
| Comp. Ex. 68 | — | compound F | 5.0 | 13 | 37 |
| Comp. Ex. 69 | — | compound T | 5.0 | 15 | 40 |
| Comp. Ex. 70 | — | compound V | 5.0 | 11 | 42 |
| Comp. Ex. 71 | — | compound Z | 5.0 | 19 | 55 |
| Comp. Ex. 72 | — | — | — | 80 | 97 |

Accumulated illuminance: 7,530 kLx · hr for 14 days and 14,180 kLx · hr for one month

TABLE 6

| | Oleum in Preparation Example 1 and Oily suspension in Preparation Example 2 | | | | Hatching Rate(%) | |
|---|---|---|---|---|---|---|
| | | UV Absorber | Antioxidant | Additive Amount (parts) | After one days | After one month |
| Example 1 | Oleum | compound (2) | compound I | 0.25 + 0.25 | 0 | 0 |
| Example 5 | Oleum | compound (3) | compound K | 0.25 + 0.25 | 0 | 0 |
| Example 10 | Oleum | compound (8) | compound B | 0.25 + 0.25 | 0 | 0 |
| Comp. Ex. 2 | Oleum | compound (2) | — | 1.0 | 0 | 87 |
| Comp. Ex. 14 | Oleum | — | compound I | 1.0 | 0 | 52 |
| Comp. Ex. 17 | Oleum | — | — | — | 0 | 100 |
| Example 21 | Oily suspension | compound (1) | compound L | 0.25 + 0.25 | 0 | 0 |
| Example 22 | Oily suspension | compound (7) | compound M | 0.25 + 0.25 | 0 | 0 |
| Example 26 | Oily suspension | compound (28) | compound I | 0.25 + 0.25 | 0 | 0 |
| Comp. Ex. 34 | Oily suspension | compound (1) | — | 1.0 | 0 | 81 |
| Comp. Ex. 42 | Oily suspension | — | compound L | 1.0 | 0 | 68 |
| Comp. Ex. 50 | Oily suspension | — | — | — | 0 | 100 |

Examination Example 6

Test of Organism Effect on Cat Flea 4 ml of diluted solution by adding water of the emulsion prepared in Preparation Example 3 or the aqueous suspension prepared in Preparation Example 4, i.e., 2 mg as etoxazole, per 1 kg of body weight was poured on the back of neck of a cat by a micro syringe. After one day of the treatment, female adult fleas were released to parasitize. Four days after the release of eggs laid by the adult fleas were collected and moved to a petri dish. The eggs were stored at 25° c. for three weeks. After that, hatching status of the eggs was observed and hatching rates were obtained.
Alternatively, after one month of the outdoor rearing of the same treated cat, female adult fleas were released in the same way as in above. Then, hatching rates of the eggs laid by the adult fleas were obtained. As seen from the results, using a UV absorber and a phenol antioxidant in combination contributes to elongation of the residual efficacy of etoxazole as compared to using either of a UV absorber or a phenol antioxidant individually.

INDUSTRIAL APPLICABILITY

The ectoparasiticide composition used on animals according to the present invention, with synergetic effect in photostabilization brought out by the UV absorber and phenol antioxidant present as components, can remarkably suppress photodecomposition of etoxazole serving as effective ingredient. Also, the combination use of the UV absorber and the phenol antioxidant does not decrease the insecticidal effect against ectoparasites. Therefore, by allowing the composition to act on animals, effect of exterminating ectoparasites by the effective ingredient can be sustained for a long period of time, thereby markedly enhancing the residual efficacy. Especially, when the composition is used in the sunlight such as outdoors, the effect is prominently expressed and therefore the composition is very useful as ectoparasiticide composition used on animals.

The invention claimed is:

1. An ectoparasiticide composition used on animals, comprising etoxazole as an active ingredient, UV absorber and phenol antioxidant;
    wherein the UV absorber is one or more compounds selected from the group consisting of benzophenone

TABLE 7

| | Emulsion in Preparation Example 3 and Aqueous suspension in Preparation Example 4 | | | | Hatching Rate(%) | |
|---|---|---|---|---|---|---|
| | | UV Absorber | Antioxidant | Additive Amount (parts) | After one days | After one month |
| Example 30 | Emulsion | Compound (2) | Compound I | 1.0 + 1.0 | 0 | 0 |
| Example 31 | Emulsion | Compound (5) | Compound O | 1.0 + 1.0 | 0 | 0 |
| Example 34 | Emulsion | Compound (16) | Compound J | 1.0 + 1.0 | 0 | 0 |
| Comp. Ex. 55 | Emulsion | Compound (16) | — | 5.0 | 0 | 82 |
| Comp. Ex. 60 | Emulsion | — | Compound J | 5.0 | 0 | 70 |
| Comp. Ex. 61 | Emulsion | — | — | — | 0 | 99 |
| Example 36 | Aqueous suspension | Compound (21) | Compound F | 1.0 + 1.0 | 0 | 0 |
| Example 37 | Aqueous suspension | Compound (22) | Compound T | 1.0 + 1.0 | 0 | 0 |
| Example 39 | Aqueous suspension | Compound (13) | Compound Z | 1.0 + 1.0 | 0 | 0 |
| Comp. Ex. 64 | Aqueous suspension | Compound (22) | — | 5.0 | 0 | 80 |
| Comp. Ex. 69 | Aqueous suspension | — | Compound T | 5.0 | 0 | 65 |
| Comp. Ex. 72 | Aqueous suspension | — | — | — | 0 | 100 | compounds represented by formula (I), cyanoacrylate compounds represented by formula (II), benzotriazole compounds represented by formula (III) and salicylic acid compounds represented by formula (IV):

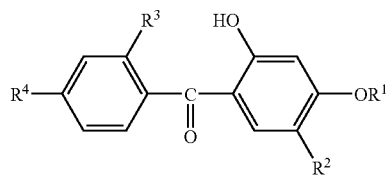
(I)

wherein $R^1$ represents a hydrogen atom, an alkyl group having 1 to 12 carbon atoms and a linear or branched chain, a benzyl group or a group represented by formula (1)

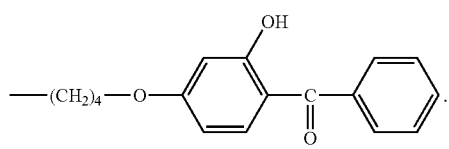
(1)

$R^2$ represents a hydrogen atom, a sulfo group ($SO_3H$) or a group represented by formula (2)

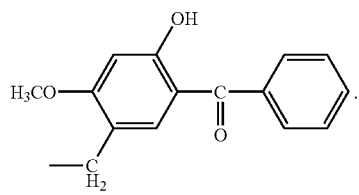
(2)

$R^3$ represents a hydrogen atom or a hydroxyl group, and $R^4$ represents a hydrogen atom or a methoxy group;

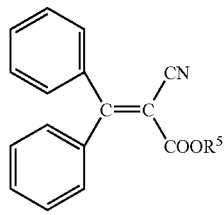
(II)

wherein $R^5$ represents an alkyl group having 1 to 8 carbon atoms and a linear or branched chain;

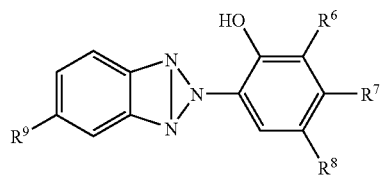
(III)

wherein $R^6$ represents a hydrogen atom, an alkyl group having 1 to 5 carbon atoms and a linear or branched chain, α,α'-dimethylbenzyl group, a group represented by formula (3) or a group represented by formula (4),

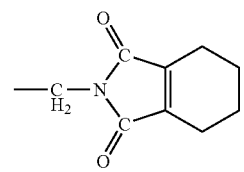
(3)

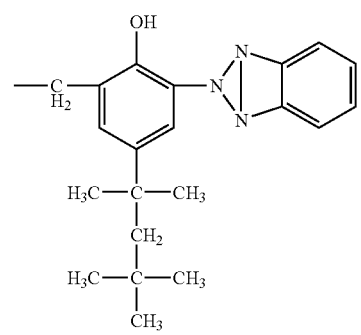
(4)

$R^7$ represents a hydrogen atom or an octoxy group, $R^8$ represents a hydrogen atom, an alkyl group having 1 to 8 carbon atoms and a linear or branched chain, a methoxy group, α,α'-dimethylbenzyl group or a methacryloxy group, $R^9$ represents a hydrogen atom or chlorine atom;

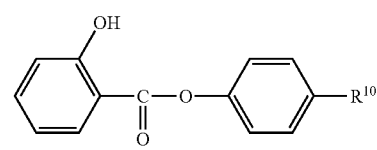
(IV)

wherein $R^{10}$ represents a hydrogen atom or a an alkyl group having 1 to 8 carbon atoms and a linear or branched chain; and wherein the phenol antioxidant is one or more compounds selected from the group consisting of a monophenol compound represented by formula (V) and the following compounds (1) to (13) which are bisphenol compounds or polyphenol compounds:

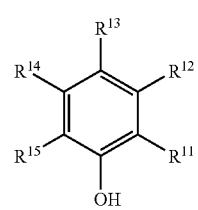
(V)

wherein $R^{11}$ represents a hydrogen atom, an isopropyl group, a chloromethyl group, a tert-butyl group, a benzyl group, 4-methylbenzyl group or a methylacrylate group; $R^{12}$ represents a hydrogen atom or a tert-butyl group; $R^{13}$ represents a hydrogen atom, a methyl group, ethyl group, a methoxy group, isooctyl propionate group or a stearyl propionate group; $R^{14}$ represents a hydrogen atom or a methyl group; $R^{15}$ represents a hydrogen atom or an alkyl group having 1 to 5 carbon atoms and a linear or branched chain;

(1) 2,2'-methylenebis(4-methyl-6-tert-butylphenol),
(2) 2,2'-methylenebis(4-ethyl-6-tert-butylphenol),
(3) 4,4'-thiobis(3-methyl-6-tert-butylphenol),
(4) 4,4'-butylidenebis(3-methyl-6-tert-butylphenol),
(5) 3,9-bis[1,1-dimethyl-2-[β-(3-tert-butyl-4-hydroxy-5-methylphenyl)propionyloxy]ethyl]-2,4,8,10-tetraoxaspiro[5.5]undecane,
(6) 2,2-thiodiethylene bis[3-(3,5-di-tert-butyl-4-hydroxypheny)propionate],
(7) triethyleneglycol bis[3-(3-tert-butyl-4-hydroxy-5-methylphenyl)propionate],
(8) 1,6-hexanediol bis[3-(3,5-di-tert-butyl-4-hydroxyphenyl)propionate],
(9) 1,1,3-tris(2-methyl-4-hydroxy-5-tert-butylphenyl)butane,
(10) 1,3,5-trimethyl-2,4,6-tris(3,5-di-tert-butyl-4-hydroxybenzyl)benzene,
(11) tetrakis[methylene-3-(3,5-di-tert-butyl-4-hydroxyphenyl)propionate]methane,
(12) tris(3,5-di-tert-butyl-4-hydroxybenzyl)isocyanurate, and
(13) bis[3,3'-bis(4'-hydroxy-3'-tert-butylpheny(butyric acid]glycol ester.

2. The ectoparasiticide composition as claimed in claim 1, wherein the blending ratio between etoxazole, UV absorber and phenol antioxidant is in terms of mass ratio, 1: from 0.05 to 5: from 0.05 to 5.

3. A method for exterminating ectoparasites, which comprises applying to the environment or administering to an animal in need of such treatment the ectoparasiticide composition as claimed in claim 1.

4. The ectoparasiticide composition as claimed in claim 1, wherein the blending ratio between etoxazole, UV absorber and phenol antioxidant is, in terms of mass ratio, 1: from 0.1 to 1: from 0.1 to 1.

5. The ectoparasiticide composition as claimed in claim 2, wherein the blending ratio between etoxazole, UV absorber and phenol antioxidant is, in terms of mass ratio, 1: from 0.1 to 1: from 0.1 to 1.

6. The ectoparasiticide composition as claimed in claim 1, wherein the blending ratio between UV absorber and phenol antioxidant is in terms of mass ratio, 1: from 0.05 to 20.

7. The ectoparasiticide composition as claimed in claim 4, wherein the blending ratio between UV absorber and phenol antioxidant is in terms of mass ratio, 1: from 0.05 to 20.

8. The ectoparasiticide composition as claimed in claim 5, wherein the blending ratio between UV absorber and phenol antioxidant is in terms of mass ratio, 1: from 0.05 to 20.

* * * * *